United States Patent
Zander et al.

(10) Patent No.: US 10,085,781 B2
(45) Date of Patent: Oct. 2, 2018

(54) CONDYLAR FRACTURE FIXATION SYSTEM

(71) Applicant: Stryker European Holdings I, LLC, Kalamazoo, MI (US)

(72) Inventors: Nils Zander, Eckernförde (DE); Manfred Wieland, Kiel (DE); Giovanni Ricciardi, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 507 days.

(21) Appl. No.: 14/640,456

(22) Filed: Mar. 6, 2015

(65) Prior Publication Data
US 2016/0256207 A1 Sep. 8, 2016

(51) Int. Cl.
| | | |
|---|---|---|
| A61B 17/84 | (2006.01) |
| A61B 17/68 | (2006.01) |
| A61B 17/72 | (2006.01) |
| A61B 17/74 | (2006.01) |
| A61B 17/86 | (2006.01) |

(52) U.S. Cl.
CPC ......... *A61B 17/84* (2013.01); *A61B 17/683* (2013.01); *A61B 17/725* (2013.01); *A61B 17/7233* (2013.01); *A61B 17/744* (2013.01); *A61B 17/8665* (2013.01); *A61B 17/8685* (2013.01); *A61B 17/8695* (2013.01)

(58) Field of Classification Search
CPC ... A61B 17/84; A61B 17/744; A61B 17/7233; A61B 17/8685
See application file for complete search history.

(56) References Cited

U.S. PATENT DOCUMENTS

| | | | |
|---|---|---|---|
| 2,489,870 A | * | 11/1949 | Dzus .................. A61B 17/683 411/339 |
| 4,796,612 A | | 1/1989 | Reese |
| 5,167,664 A | | 12/1992 | Hodorek |

(Continued)

FOREIGN PATENT DOCUMENTS

| | | |
|---|---|---|
| EP | 0827717 A2 | 3/1998 |
| GB | 2324964 A | 11/1998 |

(Continued)

OTHER PUBLICATIONS

International Search Report for Application No. PCT/US2016/020040 dated Jun. 14, 2016.

*Primary Examiner* — Christopher Beccia
(74) *Attorney, Agent, or Firm* — Lerner, David, Littenberg, Krumholz & Mentlik, LLP (57) ABSTRACT

A condylar fracture fixation system for use with an intramedullary nail includes a longitudinally extending rod having first and second ends, each end having outwardly extending threads or ridges. The rod extends along a first longitudinal axis which extends in a medial-lateral direction in use. A first and second nut is provided each nut having first and second ends. The second end of each nut having an opening formed by a plurality of resilient legs for respectively receiving the first and second ends of the rod. The second end of the first and second nuts include ridges or threads extending into the opening in each nut. The inwardly extending ridges of nuts respectively engaging the outwardly extending threads or ridges of the rod. A flexible washer is connected to the first end of each nut.

22 Claims, 5 Drawing Sheets

(56) References Cited

U.S. PATENT DOCUMENTS

| | | | |
|---|---|---|---|
| 5,250,049 A | 10/1993 | Michael | |
| 6,004,327 A | 12/1999 | Asnis et al. | |
| 6,010,505 A | 1/2000 | Asche et al. | |
| 6,302,887 B1 | 10/2001 | Spranza et al. | |
| 6,632,224 B2 | 10/2003 | Cachia et al. | |
| 6,918,912 B2 | 7/2005 | Seemann | |
| 7,347,861 B2 | 3/2008 | Johnstone | |
| 2002/0169455 A1 | 11/2002 | Bannerman et al. | |
| 2004/0122428 A1* | 6/2004 | Johnstone | A61B 17/1717 606/62 |
| 2006/0264944 A1 | 11/2006 | Cole | |
| 2007/0255315 A1* | 11/2007 | Buckman | A61B 17/08 606/218 |

FOREIGN PATENT DOCUMENTS

| | | |
|---|---|---|
| JP | H05146502 A | 6/1993 |
| WO | 02060331 A1 | 8/2002 |
| WO | 02067759 A2 | 9/2002 |
| WO | 2012116267 A2 | 8/2012 |

\* cited by examiner

CONDYLAR FRACTURE FIXATION SYSTEM

BACKGROUND OF THE INVENTION

The present invention relates to a supra condylar intramedullary nail for the femur. More particularly it relates to an intramedullary nail using a novel condylus screw having two threaded nuts or two nuts having a ratchet system and a flexible washer mounted on the nuts.

In treating a femoral fracture, it is standard practice to use a fixation device adapted to facilitate recovery of the fractured bone. The fixation device provides immobilization of the bone fragments and stabilization of the fractured femur, thus providing earlier mobilization and weight bearing of a patient. The fixation device is attached to or inserted into the femur and cooperates with the bone fragments and the femoral shaft to stabilize the bone. As the bone heals, the fixation device allows the bone fragments to compress into each other so the fragments grow together to restore the bone.

Two prevalent types of femoral fractures are supracondylar or "T-type" condylar fractures about the distal femur. A number of different fixation devices, both external and implantable, have been devised for fixation of supracondylar and condylar fractures. In the past, treatment of condylar or supracondylar fractures consisted of stabilizing the bone portions with plates and screws. However, in using plates and screws, invasive surgery is required and includes considerable dissection of the thigh in order to expose the fracture so as to attach the plates and screws. The resultant devasculariztion of the distal portion of the femur has lead to a high frequency of complications of delayed union of the bone sections, osseous fracture and infection. Additionally, due to the muscular stresses in the region of the condylus and supracondylus, the treatment may involve undesirable post-operative procedures and complications including the bending or breaking of the plates, loosening of the screws and migration of the femoral shaft.

Intramedullary (IM) nailing has become a standard procedure for treating supracondylar and condylar fractures. In its basic form, IM nailing consists of driving a rod-like nail into the intramedullary bone canal of the femur to stabilize transverse fractures of the femur. To further stabilize the bone fragments interlocking cross-bolts or screws through the nail that are fixed on both sides of the fracture are used.

Known IM nails have been designed for treatment of condylar and supracondylar fractures. U.S. Pat. No. 6,010,505 Asche et al., the disclosure of which is herein incorporated by reference in its entirety, discloses an intramedullary device having an IM nail and interlocking bolts or screws to grip and stabilize the femoral condyles with respect to the femoral shaft.

Figure 1:
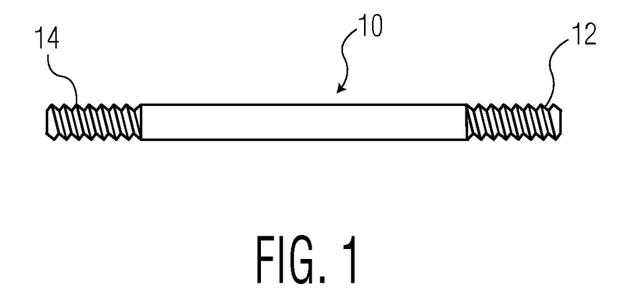
FIG. 1 is an elevation view of the rod of the present invention having a pair of threaded ends.
Figure 1A:
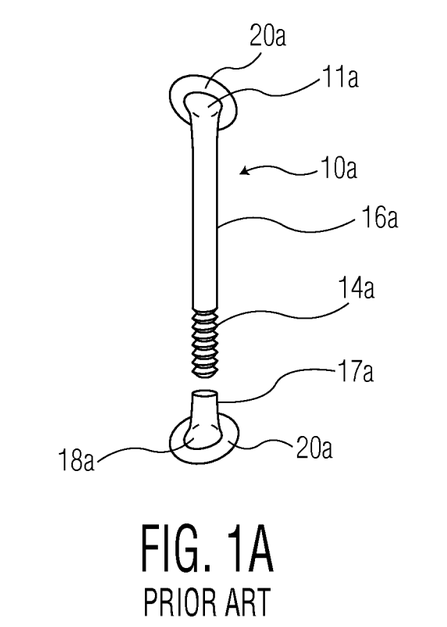
FIG. 1A is an isometric view of the prior art condylar screw having a nut, washer and a single threaded end.

In Femoral fractures involving the femoral condyles (e.g. T-condylar Fractures), an IM nail is currently used in combination with a Stryker Trauma T2 condyle screw (shown in FIG. 1A (prior art)) in order to realign, compress and fix the femoral condyle fracture fragments. The existing condyle screw system consists of one 5 mm diameter screw with a first pre-assembled 15 mm diameter washer at the level of the screw head (the washer position is fixed to the screw adjacent the head in a manner such that it is free to rotate in all directions). A second nut with a pre-assembled 15 mm diameter washer mounted thereon can threadably engage threads on the end of the screw opposite the head, (the washer position is fixed to the nut but, again, it is free to rotate in all directions).

In the prior art design once the screw is completely inserted into the bone medially, the nut is then screwed onto the screw laterally, a compression force will be generated between the washer and the bone cortex from both sides (lateral and medial). This compression force fixes the bone fragments. All the components (screw, nut, washers) are preferably made out of a titanium alloy, preferably grade 5. When the prior art condyle screw is used on an irregular-shaped-surface of the distal femoral condyles, the washers might not properly adapt to the cortical surface. As a result, the washer might protrude out the bone surface and impinge to the biological tissue. The impingement may involve the knee joint cartilage surface, generating pain, inflammation or even damage to the tibial plate cartilage. Furthermore the procedure to compress the fragments is time-consuming since many screw turns need to be carried out in order to achieve the contact of both washers (from both sides) to the bone cortex.

BRIEF SUMMARY OF THE INVENTION

In the preset invention, a condylar fracture fixation system includes an intramedullary (IM) nail which, after insertion into the femur extends in a proximal-distal direction. A condylar screw system includes a longitudinally extending rod which has first and second ends with each end having outwardly extending threads or ridges. The rod extends along a first longitudinal axis extending in a medial-lateral direction when inserted through the femoral condyles and the IM nail.

A first and second nut each having first and second ends are provided. The second end of each nut has an opening for respectively receiving the first and second ends of the rod. The second end of the first and second nuts include threads or ridges extending radially inward into an opening in each nut. The inwardly extending threads or ridges of the first and second nuts respectively engaging the outwardly extending threads or ridges of the rod first and second ends. Preferably the first end of each nut is a cylindrical body having two, three or over four legs extending towards the second end of each nut. At least two of the legs have threads or ridges extending into the opening of each nut.

A flexible washer engages the first end of the first and second nuts. Like the prior art screw, the washers are axially fixed to each nut in a manner which permits rotation about the rod longitudinal axis. The radially outwardly extending threads of the first and second rod ends may be formed as a helical thread. The radially inwardly extending threads of the first and second nuts may also be formed as helical threads. The flexible washer and nut may be a one-piece construct or may be separate but connected in a manner which allows the washer to rotate around the axis of the nut. This may be accomplished by allowing the washer to snap into a circumferential groove formed at the outer surface of the first end of the nut. The nut and washer may be made of a material selected from the group consisting of a polymeric material, titanium, a titanium alloy and stainless steel. The flexible washer may be made of metal (Titanium) having a thickness of 1 to 3 mm.

The first and second nuts preferably have a body portion at the first end with a plurality of legs extending outwardly therefrom towards the second end. The legs surround a central opening for receiving the threaded rod. The ridges or threads are located on inner surfaces of the legs. The nut body portion may be threaded into the threaded rod or if ridges are present, or may be moved axially onto the rod without rotation since the two, three or four legs are designed to flex outwardly. Thus the nuts can slide over the threads or ridges on each end of the nail for example, as in a ratchet system. The flexible or bendable washer may be non-circular such as having two diametrically opposed oval positions similar to a pair of oval opposed petals of a flower or leafs of a plant, or a two-blade propeller on a plane. Two opposed pairs are preferred since minimum coverage of the bone is preferred and using three or four "leafs" large enough to be effective teaches away from the medical need of "minimum coverage" at the condlyes. Both washers, petal, and leaf portions are bendable by hand or with a hand tool so that the surgeon can form-fit them to the patient condyles.

One important aspect of this design is, that the washer surface is reduced to a minimum so it covers the bone only where needed and does not protrude outwardly.

The nut can have a body portion and the washer could be one piece construct manufactured as a molded plastic part, however, although a snap-filled metal washer (Titanium) is preferred.

If a one-part nut washer would be applied then the connection between the washer opposed oval petals or leafs and the washer body would be preferably made by injection moulding of plastic and alternatively laser welding or glueing of metal.

Alternatively a two-part nut washer could also be formed by a circumferential groove on the washer body so that a washer with two opposed petals or propeller wings can be clamped onto the washer body portion 38. This is how the prior art T2 Condyle Washer is assembled.

Alternatively the condylar fracture fixation system may not include an IM nail but also have a longitudinally medially-laterally extending rod having first and second ends. The first and second ends each having a plurality of radially outwardly extending protrusions such as ridges or threads. First and second nuts are provided with each nut having a hollow interior open portion having an open free end for respectively receiving the first and second ends of the rod. The interior portion of the first and second nuts having a plurality of recesses for receiving the outwardly extending protrusions on the first and second ends of the rod. A flexible washer is mounted on an end of each of the first and second nuts opposite the open end.

DETAILED DESCRIPTION

Referring to FIG. 1 there is shown a threaded rod generally denoted as 10 having a first and second threaded end 12 and 14. Rod 10 can be of any length in diameter typically being a 5 mm diameter rod with a variety of lengths. Rod 10 forms the shaft of a condylar screw used to compress fractures of the distal femur.

FIG. 1A shows a prior art condylar screw generally denoted as 10a having a head 11a formed at a first end of a shaft 16a, having a threaded end 14a. A nut 17a has internal threads adapted to threadably engage threads 14a on shaft 16a. Nut 17a includes an enlarged head portion 18a. A washer 20a is attached to each head portion 11a, 18a and is free to rotate with respect to shaft 16a. Washers 20a are made of metal and are not easily deformable.

Figure 2:
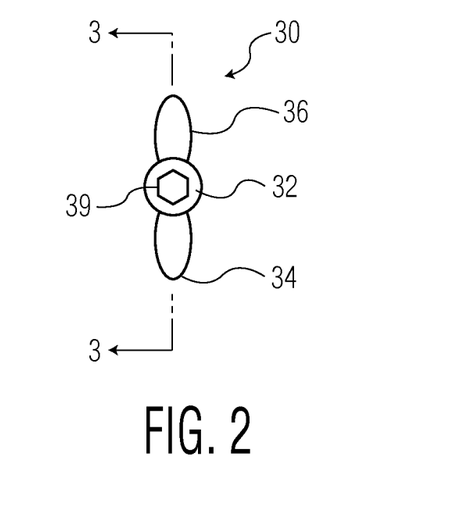
FIG. 2 is a top view of the washer and nut combination of the present invention.
Figure 3:
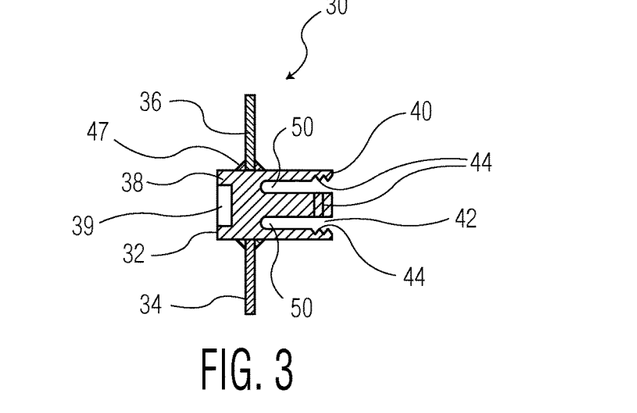
FIG. 3 is a cross-sectional view of the washer and nut combination of FIG. 2 with flexible titanium washers welded onto the nut body.

Referring to FIGS. 2 and 3, there is shown a nut 18 and washer 20 combination generally denoted as 30, which includes a nut body portion 32 and two flexible portions 34 and 36. Preferably flexible washer portions 34 and 36 are in the shape of a flower petal or oblong shape spaced on opposite sides of nut 32, i.e. 180° apart. Three or four such petal-like flexible washer portions may be utilized spaced equidistantly around the circumference of nut body 32. Nut body 32 includes a solid body portion 38 from which extends a plurality of legs 40. Preferably, there are four legs 40 as shown in FIG. 3, surrounding a hollow or open interior 42 of nut and washer 30 designed to receive a threaded ends 12, 14 of rod 10. Legs 40 have inwardly extending ridges or threads 44 which engage with the thread of threaded ends 12, 14. The washer and nut 30 may have two or three legs if desired. FIG. 3 shows a pair of titanium leafs or pedal-like washer portions welded to a titanium nut body.

Figure 2A:
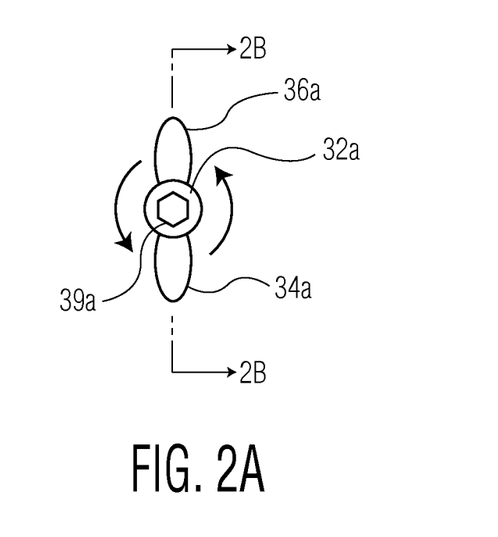
FIG. 2A is a top view of the washer and nut combination of FIG. 2 showing the rotatability of two flexible portions mounted on the washer of the present invention.

Referring to FIG. 2A, there is shown the nut washer combination of FIG. 2 with two oval washer portions 34a and 36a rotatably mounted on nut solid body portion 38a. Also shown is a hex portion 39a used to drive the nut body 32a onto the threaded rod 10.

Figure 2B:
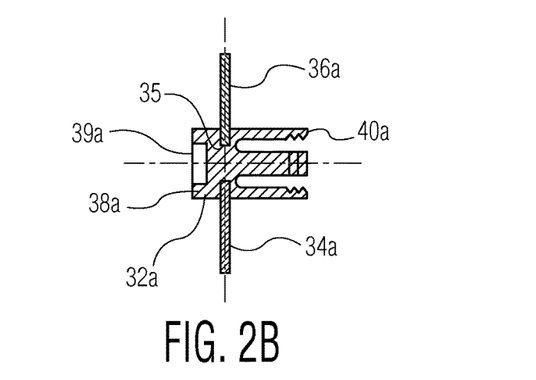
FIG. 2B is a cross-sectional view of FIG. 2A along lines 2B-2B showing the washer with the flexible washer portions rotatably mounted in a groove in the washer body.

FIG. 2B shows a cross-sectional view of FIG. 2A along lines 2B-2B with the nut body 32 including a groove 35 for receiving inner ends of washer portions 34a and 36a. Preferably, portions 34a and 36a are integrally formed on an inner ring-like portion which is received within a circumferential groove 35. At least a major portion of the circumferential groove 35 extends around the nut solid body portion 38a. The ring may act as a snap ring by having part of the ring-like portion open so that the open portion may be elastically made larger to fit and snap into the groove 35. Since the elastic deformation is resilient, the ring will snap into position, thus holding portions 34a, 36a on nut body 32a, but allowing the rotation thereof around the circumference of the preferably cylindrical nut body 32a. Preferably, the groove 35 is formed in the solid body portion 38a intermediate the drive portion 39a and the legs 40a.

Figure 2C:
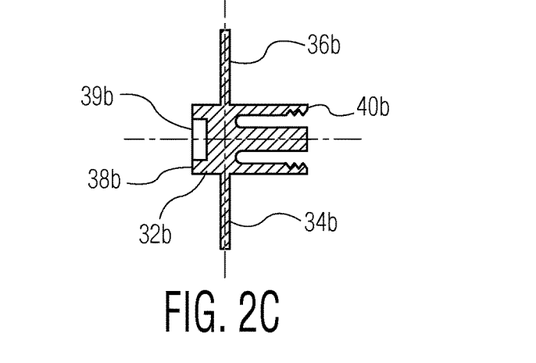
FIG. 2C is a cross-sectional view similar to that of FIG. 2B, but with the flexible washer portions integrally formed on the nut body such by injection molding.

Referring to FIG. 2C, there is shown a nut 32b having a solid body portion 38b, a drive portion 39b, legs 40b and a pair of integrally formed washer portions 34b and 36b. Washer portions 34 and 36b may be injection molded along with the nut body 32b. This embodiment may be made of a polymer such as PEEK (polyetheretherketone). FIG. 3 shows a titanium nut 32 with a pair of titanium flexible portions 34 and 36 welded to solid body portion 38. Obviously, the flexible portions 34 and 36 do not rotate about the circumference of nut 32 in this embodiment.

Flexible washer portions 34, 36 are preferably coupled to nut solid body portion 38 by a snap fit connection. In the preferred embodiment, the washer portions 34, 36 are made of titanium approximately 1 mm thick. In the preferred embodiment, the legs 40 are separated by slots 50, which are approximately 1 mm wide and 4 mm long. Legs 40 are approximately 1 mm thick and are able to flex outwardly upon engagement between teeth or ridges 42 and the threaded ends 12, 14 of rod 10. While ridges 42 may be concentric parallel protrusions extending into the hollow interior of nut 30, such could be formed as helical threads.

Figure 4:
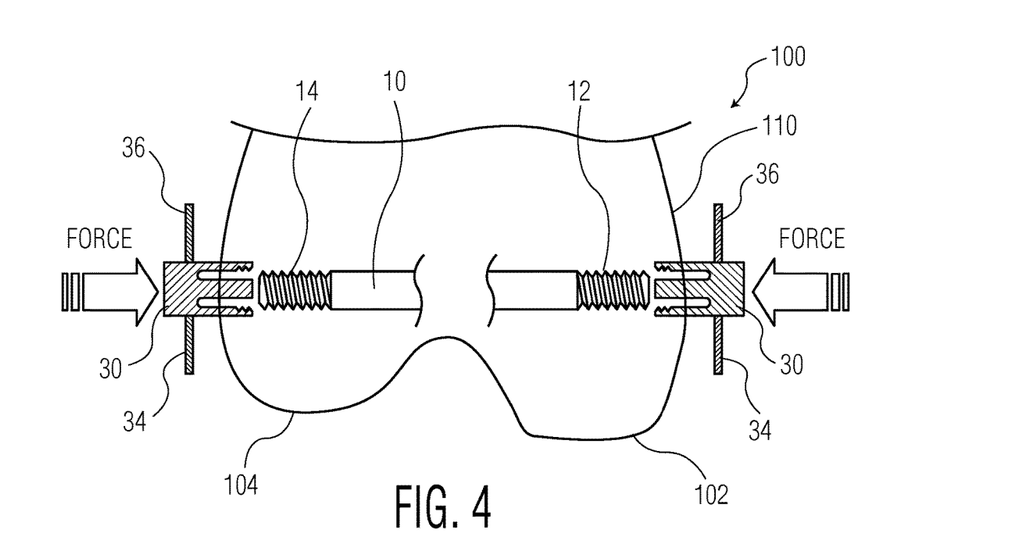
FIG. 4 is a schematic view of a pair of nuts including the washers as shown in FIGS. 2 and 3 pressed or threaded onto the threaded ends of the rod of FIG. 1.
Figure 5:
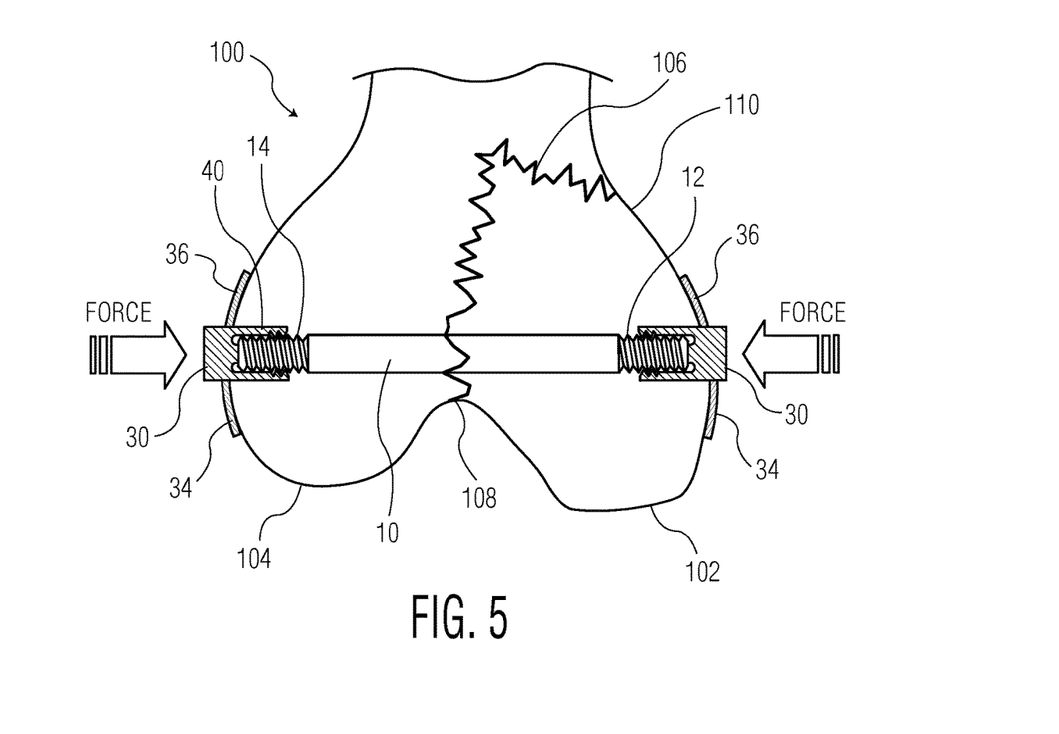
FIG. 5 shows the two nut/washer combination elements fully seated on the threaded ends of the rod of FIG. 1 compressing a condylar fracture in a femur.

Referring to FIGS. 4 and 5, there is shown the method of using the condylar fixation system of the present invention which includes inserting rod 10 into the distal femur denoted as 100 across the medial and lateral condyles 102, 104. Typically, the fracture 106 occurs at the inter-condylar notch area 108 and extends proximally and laterally to the medial condyle area 110.

As shown in FIG. 4, the pair of nuts and flexible portions 36 may be inserted from the medial and lateral sides of the distal femur into engagement with the threaded portions 12, 14 of rod 10. This may be done by applying an axial force as shown in FIGS. 4 and 5 pushing nuts 32 and flexible portions 30 onto the threaded ends of rod 10. Alternately, if the ends of rod 10 and the protrusions 44 of nut legs 40 are helical threads, nut and flexible portions 30 may be screwed onto position as a typical nut.

Figure 6:
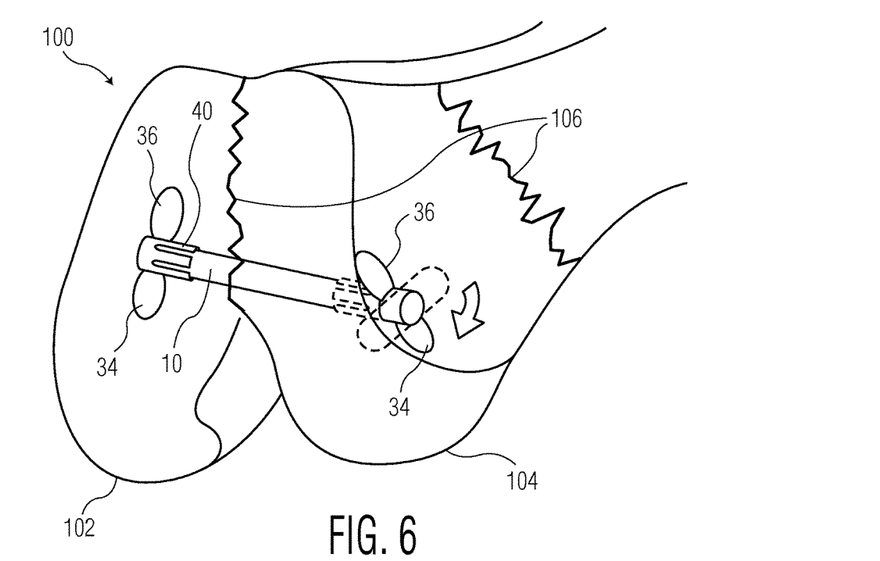
FIG. 6 shows an isometric view of a distal femur with the condylar screw of the present invention compressing a condylar fracture.

Referring to FIG. 5, there is shown nuts/flexible portions 30 in the seated position with legs 40 fully engaging threaded portions 12, 14 of rod 10. In this position, oval washer portions 34 and 36 deform upon engagement with the outer cortex of condyles 102, 104 to match the surface contour. Oval washer portions 34, 36 are mounted on nut body 32 in such a manner that they may rotate about the central axes of the nut but are fixed axially. Thus they may be positioned in any circumferential orientation which allows oval portions 34, 36 to best conform with the outer bone surface in the condylar area. The final assembly is shown in FIG. 6 with the condylar screw of the present invention compressing fracture 106.

Figure 7:
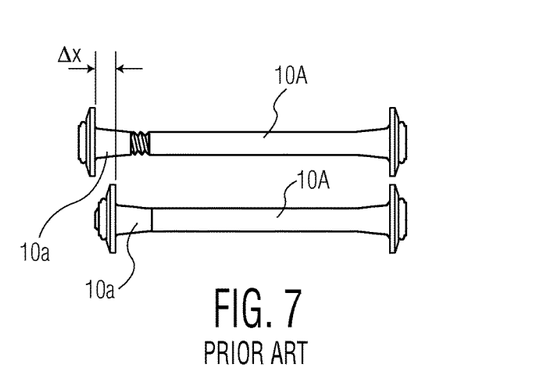
FIG. 7 is an elevation view of the prior art condylar screw of FIG. 1A showing the possible fracture compression distance $\Delta x$.
Figure 8:
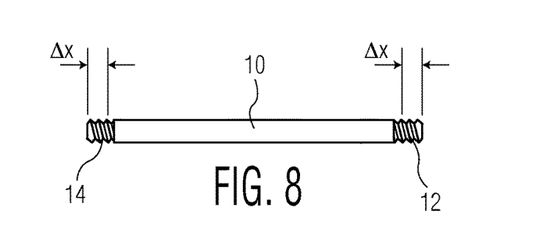
FIG. 8 shows the possible fracture compression distance $2 \Delta x$ with the condylar screw of the present invention.

Referring to FIGS. 7 and 8, there is shown a comparison of the compression range of the use of two nuts 30 on a threaded rod 10 of the present invention instead of a single screw as shown in FIGS. 1A and 7. The use of a pair of nuts 32 doubles the compression range $\Delta x$ of FIG. 7 to 2 $\Delta x$ of FIG. 8. As a result the condylar screw of the present invention will reduce the number of different screw lengths needed to be kept in inventory while ensuring the same working range.

The device of the present invention may be used for fracture stabilization in general where compression between implant and bone is desired. For example, the device can be used in the proximal humerus for small fragments, osteoporosis and where there is a relatively thin cortex where a washer is beneficial; the radius/ulna; the pelvis in the sacroiliac joint; the proximal and distal tibia; and the foot in the calcaneous and charcot plate Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fracture fixation system comprising:
   a longitudinally extending rod having first and second ends, each end having outwardly extending ridges, the rod extending along a first longitudinal axis;
   a first and second nut each having first and second ends, the second end of the first and second nuts each having an opening for respectively receiving the first and second ends of the rod, the first and second nuts each having a body portion at the first end with at least two legs separated by slots and extending from the body portion towards the second end of the nut and surrounding the opening, the second end of the first and second nuts each including ridges located on inner surfaces of the legs and extending into the opening in each nut, the legs being capable of flexing outwardly of the nut opening to allow movement of the first and second nuts onto the rod without rotating the nuts, the inwardly extending ridges of the first and second nuts respectively engaging the outwardly extending ridges of the rod first and second ends when the first and second nuts are assembled in the first and second ends of the rod, respectively; and
   a washer having opposed bendable portions engaging the first end of both the first and second nuts.

2. The fracture fixation system as set forth in claim 1 wherein the radially outwardly extending ridges of the first and second rod ends are formed as a helical thread.

3. The fracture fixation system as set forth in claim 2 wherein the radially inwardly extending ridges of the first and second nut are formed as helical threads.

4. The fracture fixation system as set forth in claim 1 wherein the flexible washer and nut are connected.

5. The fracture fixation system as set forth in claim 4 wherein the washer and nut construct is made of a material selected from the group consisting of a polymeric material, titanium, a titanium alloy and stainless steel.

6. The fracture fixation system as set forth in claim 1 wherein the flexible washer is made of metal having a thickness of 1 to 3 mm.

7. The fracture fixation system as set forth in claim 1 wherein the at least two legs include four legs.

8. The fracture fixation system of claim 1 wherein the flexible washer is non-circular.

9. The fracture fixation system of claim 8 wherein the flexible washer has two diametrically opposed oval portions.

10. The fracture fixation system as set forth in claim 1 wherein the body portion of each nut has a circumferential groove for receiving an inner surface of each washer.

11. The fracture fixation system as set forth in claim 1 further comprising an intramedullary nail having a bore for receiving the longitudinally extending rod.

12. A fracture fixation system comprising:
   a longitudinally extending rod having first and second ends, the first and second ends having a plurality of radially outwardly extending protrusions;
   first and second nuts each having first and second ends, the second end of the first and second nuts including a hollow interior portion having an open end for receiving the first and second ends of the rod, the first and second nuts each having a body portion at the first end with first and second deflectable legs separated by slots and extending from the body portion towards the second end of the nut and surrounding the open end, an interior portion of the first and second deflectable legs of the first and second nuts having a plurality of recesses located on inner surfaces of the legs for receiving the outwardly extending protrusions on the first and second ends of the rod, the legs being capable of flexing outwardly of the nut opening to allow movement of the first and second nuts onto the rod without rotating the nuts, the inwardly extending recesses of the first and second nuts respectively engaging the outwardly extending protrusions of the rod first and second ends when the first and second nuts are assembled in the first and second ends of the rod, respectively;

a flexible washer mounted on the first end of each of the first and second nuts opposite the open end.

13. The fracture fixation system as set forth in claim 12, wherein the radially outwardly extending protrusions of the first and second rod ends are formed as a helical thread.

14. The fracture fixation system as set forth in claim 13 wherein the radially inwardly extending recesses of the first and second nut are formed as helical threads.

15. The fracture fixation system as set forth in claim 12 wherein the flexible washer and nut are connected together.

16. The fracture fixation system as set forth in claim 15 wherein the nut and washer are a one-piece construct made of a material selected from the group consisting of a polymeric material, titanium, a titanium alloy and stainless steel.

17. The fracture fixation system as set forth in claim 12 wherein the flexible washer is made of metal having a thickness of 1 to 3 mm.

18. The fracture fixation system as set forth in claim 12 wherein the first and second deflectable legs include four deflectable legs.

19. The fracture fixation system of claim 12 wherein the flexible washer is non-circular.

20. The fracture fixation system of claim 19 wherein the flexible washer has two diametrically opposed oval portions.

21. The fracture fixation system as set forth in claim 12 wherein the body portion of each nut has a circumferential groove for receiving an inner surface of each washer.

22. The fracture fixation system as set forth in claim 12 further comprising an intramedullary nail having a bore for receiving the longitudinally extending rod.

* * * * *